United States Patent [19]

Verbrugge et al.

[11] Patent Number: 5,189,197
[45] Date of Patent: Feb. 23, 1993

[54] PROCESS FOR PREPARING CARBAMATES, AND INTERMEDIATES THEREIN

[75] Inventors: Pieter A. Verbrugge; Jannetje De Waal, both of Amsterdam, Netherlands

[73] Assignee: Shell Internationale Research Maatschappij B.V., Netherlands

[21] Appl. No.: 485,550

[22] Filed: Feb. 27, 1990

[30] Foreign Application Priority Data

Mar. 13, 1989 [GB] United Kingdom ............... 8905741

[51] Int. Cl.$^5$ .......................................... C07C 271/62
[52] U.S. Cl. ...................................... 560/24; 560/29; 560/30; 560/31; 560/32; 564/133
[58] Field of Search ...................... 560/24, 29, 30, 31, 560/32; 564/133

[56] References Cited

U.S. PATENT DOCUMENTS

| | | |
|---|---|---|
| 4,457,943 | 7/1984 | Becher et al. |
| 4,595,533 | 6/1986 | Thompson ............... 560/24 |

FOREIGN PATENT DOCUMENTS

| | | |
|---|---|---|
| 158248 | 3/1983 | European Pat. Off. |
| 161019 | 11/1985 | European Pat. Off. |
| 174274 | 3/1986 | European Pat. Off. |
| 219460 | 8/1987 | European Pat. Off. |
| 1324293 | 7/1973 | United Kingdom |
| 2163430 | 2/1986 | United Kingdom ............... 564/133 |

*Primary Examiner*—Jose G. Dees
*Assistant Examiner*—Deborah D. Carr

[57] ABSTRACT

The invention provides a process for the preparation of N-benzoylcarbamates of general formula

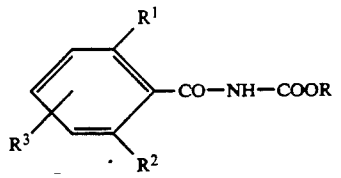

wherein $R^1$ represents a hydrogen atom, a halogen atom, a $C_{1-4}$ alkyl group, a $C_{1-4}$ alkoxy group or a trifluoromethyl group, $R^2$ represents a halogen atom, a $C_{1-4}$ alkyl group, a $C_{1-4}$ alkoxy group or a trifluoromethyl group, $R^3$ represents a hydrogen atom, a halogen atom, a methyl group or a trifluoromethyl group, and R represents a $C_{1-8}$ alkyl group optionally substituted by one or more halogen atoms or a phenyl group optionally substituted by one or more substituents selected from halogen atoms and methyl groups, characterized by reacting an alkali metal salt of a benzamide of general formula

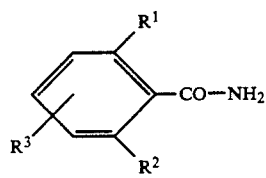

wherein $R^1$, $R^2$ and $R^3$ are as defined above, with a carbonate of formula

RO—CO—OR  (III)

wherein R is as defined above, in the presence of an inert solvent, and neutralizing the resulting alkali metal salt of the compound of formula I; and (intermediate) alkali metal salts of the compounds of formula I.

7 Claims, No Drawings

PROCESS FOR PREPARING CARBAMATES, AND INTERMEDIATES THEREIN

This invention relates to processes for the preparation of carbamates, in particular N-benzoylcarbamates, and to intermediates in such preparation.

UK Patent Specification No. 1,324,293 discloses a class of compounds of formula

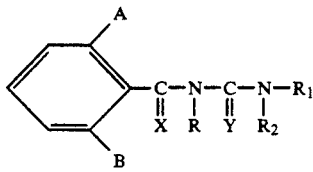

wherein A is a hydrogen atom, a halogen atom, a methyl group or a methoxy group, B is a hydrogen atom, a halogen atom, a methyl group or a methoxy group, with the proviso that A and B do not both represent a hydrogen atom, X and Y may both be oxygen atoms, R and $R_1$ may both be hydrogen atoms, and $R_2$ represents inter alia a substituted phenyl group, and their use as insecticides.

The compound of the above formula wherein A and B are both fluorine atoms, X and Y are both oxygen atoms, R and $R_1$ are both hydrogen atoms and $R_2$ is 4-chlorophenyl is the insecticide diflubenzuron (N-(4-chlorophenyl)-N'-(2,6-difluorobenzoyl)urea) and the corresponding compound wherein $R_2$ is 4-trifluoromethylphenyl is the insecticide penfluron (N-(2,6-difluorobenzoyl)-N'-(4-trifluoromethylphenyl)urea.

U.S. Pat. No. 4,457,943 discloses, inter alia, N-(2,4-difluoro-3,5-dichlorophenyl)-N'-(2,6-difluorobenzoyl) urea, the insecticide known as teflubenzuron. EP-A-161019 discloses, inter alia, N-(2,6-difluorobenzoyl)-N'-(2-fluoro-4-[2-chloro-4-(trifluoromethyl) phenoxy]phenyl urea, the insecticide/miticide known as flufenoxuron.

One method proposed in UK Patent Specification No. 1,324,293 for the preparation of the compounds of the above formula wherein R and $R_1$ are both hydrogen comprises reacting an O-ethylcarbamate compound of formula

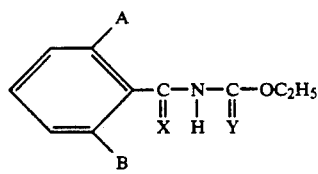

with a compound of formula $R_2$—$NH_2$ (Page 11 lines 13 to 18). It is stated (Page 14 lines 25 to 29) that this reaction takes place in the presence of a solvent. Examples of suitable solvents are xylene, toluene, chlorobenzene and other similar solvents having a boiling point higher than about 100° C. The reaction is carried out at a temperature which is about equal to the boiling point of the solvent used. Example 10 describes the preparation of N-(2,6-dichlorobenzoyl)-N'-(3,4-dichlorophenyl)urea in this manner, in 90% yield, using xylene as solvent. There is no description of the preparation of the O-ethylcarbamates.

Ep-A-174274, EP-A-219460 and GB-A-2163430 all disclose classes of N-benzoylcarbamates and their use in preparing various N-benzoyl-N-phenylureas having insecticidal activity by reaction with the appropriate substituted aniline. For example, GB-A-2163430 discloses N-benzoyl-carbamates of formula

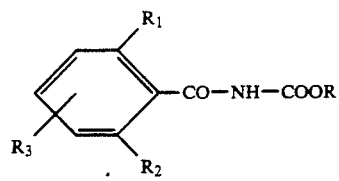

wherein $R_1$ is hydrogen, halogen, $CF_3$ or $C_{1-4}$ alkoxy, $R_2$ is halogen, $C_{1-4}$ alkyl, $CF_3$ or $C_{1-4}$ alkoxy, $R_3$ is hydrogen, halogen, $CF_3$ or methyl and R is a $C_{1-8}$ alkyl radical which may be substituted by halogen, preferably by chlorine. These N-benzoyl-carbamates are described as being obtainable in a manner known per se by reacting the appropriate benzoyl isocyanate with a suitable alcohol or by reacting the appropriate benzamide, in the presence of a base, with an appropriate ester of chloroformic acid (Page 3 lines 26 to 28).

It has now surprisingly been found possible to prepare N-benzoylcarbamates in high yield by a route which avoids the use, on the one hand, of benzoylisocyanates and, on the other hand, of chloroformic acid esters.

According to the present invention therefore there is provided a process for the preparation of N-benzoylcarbamates of general formula

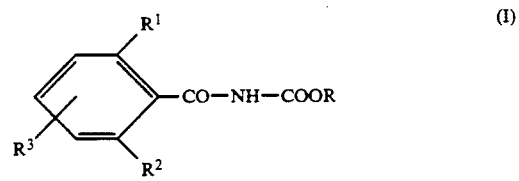

wherein $R^1$ represents a hydrogen atom, a halogen atom, a $C_{1-4}$ alkyl group, a $C_{1-4}$ alkoxy group or a trifluoromethyl group, $R^2$ represents a halogen atom, a $C_{1-4}$ alkyl group, a $C_{1-4}$ alkoxy group or a trifluoromethyl group, $R^3$ represents a hydrogen atom, a halogen atom, a methyl group or a trifluoromethyl group, and R represents a $C_{1-8}$ alkyl group optionally substituted by one or more halogen atoms or a phenyl group optionally substituted by one or more substituents selected from halogen atoms and methyl groups, characterised by reacting an alkali metal salt of a benzamide of general formula

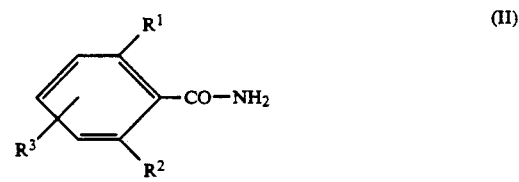

wherein $R^1$, $R^2$ and $R^3$ are as defined above, with a carbonate of formula

RO—CO—OR (III)

wherein R is as defined above, in the presence of an inert solvent, and neutralising the resulting alkali metal salt of the compound of formula I.

In formulae I and II, it is preferred that $R^1$ is a hydrogen, fluorine or chlorine atom, $R^2$ is a fluorine or chlorine atom and $R^3$ is a hydrogen atom. Most preferably, $R^1$ and $R^2$ are both fluorine atoms.

In formulae I and III, R is preferably a $C_{1-6}$ alkyl group, conveniently a $C_{1-4}$ alkyl group such as methyl or ethyl, or a phenyl group.

Compounds of formula II are either known compounds, as disclosed in UK Patent Specification No. 1,324,293, U.S. Pat. No. 4,457,943, EP-A-161019, EP-A-174274, EP-A-219460 or GB-A-2163430 discussed above, or may be made by analogous methods to those used for making the known compounds.

Compounds of formula III are also either known materials or may be prepared in analogous manner to those for preparing known materials. For example, dimethyl carbonate, diethylcarbonate, diphenyl carbonate and dipropyl carbonate are commercially available, e.g. ex Aldrich Chemie N.V., Brussels, Belgium.

The alkali metal salt of the benzamide of formula II may conveniently be generated from the benzamide using an alkali metal base, e.g. a hydride or hydroxide of an alkali metal, preferably of lithium, sodium or potassium. Depending on the nature of the inert solvent, which may be a mixture of solvents, the alkali metal salt may in some cases be generated in situ from the alkali metal itself.

The optimal reaction temperature will depend inter alia on the nature of the carbonate of formula III and the nature of the inert solvent. The reaction may conveniently be effected at a temperature in the range 0° C. to the distillation temperature of the reaction mixture.

Suitable inert solvents are ketones such as acetone and methyl ethyl ketone esters such as ethyl acetate, secondary alcohols such as 2-butanol, chlorinated hydrocarbons such as dichloroethane or methylene chloride, ethers such as tetrahydrofuran, aliphatic hydrocarbons such as cyclohexane, and aromatic solvents such as benzene, toluene, xylene or chlorobenzene.

Preferably the molar ratio of compound of formula III to compound of formula II is from 1:1 to 2:1.

In some instances when the inert solvent does not comprise a secondary alcohol, it may be found to be advantageous to initiate reaction by addition of a small amount of a secondary or tertiary hydroxy compound such as isopropanol, tertiary butanol or ricinoleic acid.

The order of mixing of the reactants is in general not critical. However, where the alkali metal base used to generate the alkali metal salt of the benzamide of formula II is a hydroxide, the base is added to the compound of formula II and water is eliminated before addition of compound of formula III. Preferably the molar ratio of alkali metal base to compound of formula II is from 1:1 to 1.5:1.

The alkali metal salts of the compounds of formula I may if desired be isolated, or they may be neutralised without isolation.

The neutralisation of the resulting alkali metal salt of the compound of formula I may conveniently be effected by treatment of the salt with an aqueous acid, e.g. aqueous hydrochloric, sulphuric, formic or acetic acid. Neutralisation may conveniently be effected at a temperature in the range from ambient temperature to distillation temperature of the reaction mixture.

The present invention also provides N-benzoylcarbamate, alkali metal salts, per se, of general formula

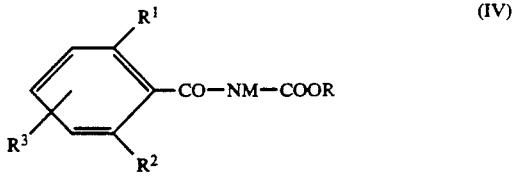

(IV)

wherein M is a lithium, sodium or potassium atom, and $R^1$, $R^2$, $R^3$ and R are as defined above.

The invention will be further understood from the following illustrative Examples.

EXAMPLE 1

Preparation of N-2,6-difluorobenzoyl-O-methylcarbamate 2,6-Difluorobenzamide (79.5 g, 0.5 mol), dimethylcarbonate (67 g, 0.76 mol) and acetone (250 ml) were stirred together at 0° C. Sodium hydride (16.6 g, 0.69 mol) was added. Reaction was monitored by collection and measurement of hydrogen. After 2 hours, during which 13 liters of hydrogen were collected, the reaction mixture was allowed to warm to ambient temperature (20° C.) and when evolution of hydrogen ceased, formic acid (98%, 35 g) was added. Further hydrogen evolved, to an overall total of 15 liters. The resulting mixture was filtered, to remove precipitated sodium formate, and the resulting acetone solution was evaporated to yield N-2,6-difluorobenzoyl-O-methylcarbamate as a white solid (109 g, 97%, 97.2% pure by high performance liquid chromatography (HPLC), the remainder being difluorobenzamide).

NMR, in CDCl$_3$, delta (ppm): 3.75,s,3H; 6.95,m,2H; 7.40,m,1H; 8.7,s,1H.

EXAMPLE 2

Preparation of N-2,6-difluorobenzoyl-O-methylcarbamate 2,6-Difluorobenzamide (79.5 g, 0.5 mol), dimethylcarbonate (67 g, 0.76 mol) and ethyl acetate (250 ml) were stirred together at 0° C. Sodium hydride (16.6 g, 0.69 mol) was added, followed by isopropanol (30 g) to initiate evolution of hydrogen. Reaction was monitored by collection and measurement of hydrogen, as in Example 1. When evolution of hydrogen ceased at 0° C., the reaction mixture was allowed to warm to ambient temperature (20° C.) and formic acid (35 g) was added. After evolution of hydrogen ceased, and after filtration to remove precipitated sodium formate, solvent was evaporated off to yield crude product as a white solid (106 g). The crude product was added to 170 ml toluene and warmed until a clear solution was obtained. On cooling to ambient temperature, a white solid precipitated out and was filtered to give pure N-2,6-difluorobenzoyl-O-methylcarbamate (92 g, 85.5%), m.p. 123° to 123.5° C.

EXAMPLE 3

Preparation of N-2,6-difluorobenzoyl-O-methylcarbamate 2,6-Difluorobenzamide (79 g, 0.5 mol), dimethylcarbonate (65 g, 0.72 mol) and 1,2-dichloroethane (250 ml) were stirred together at ambient temperature (20° C.), and sodium hydride (16.8 g, 0.7 mol) was added, followed by isopropanol (30 g) to initiate evolution of hydrogen. The mixture was cooled to 0° C. and reaction was monitored by collection and measurement of hydrogen as in Example 1. During collection of the first 10 liters of hydrogen, severe frothing of the reaction mixture was observed. After 12.3 liters of hydrogen had evolved, reaction ceased, formic acid was added and the reaction mixture was heated to reflux temperature. After evolution of hydrogen ceased, and filtration (at 80° C.) to remove precipitated sodium formate, solvent was evaporated off to yield crude product as a white solid (106 g, 94% pure by HPLC). Recrystallisation from toluene (170 ml) yielded pure N-2,6-difluorobenzoyl-O-methylcarbamate (99.7 g, 93%) m.p.123° to 123.5° C.

EXAMPLE 4

Preparation of
N-2,6-difluorobenzoyl-O-methylcarbamate 2,6-Difluorobenzamide (79.2 g, 0.5 mol), dimethyl carbonate (65 g, 0.72 mol) and 2-butanol (250 ml) were stirred together at 0° C., and sodium hydride (16.8 g, 0.7 mol) was added. After 12 liters of hydrogen had evolved, reaction ceased, the reaction mixture was allowed to warm to ambient temperature (20° C.) and formic acid (32.5 g) was added. The mixture, which was in the form of a thick slurry, was heated to 80° C. and filtered (at 80° C.) to remove precipitated sodium formate. Evaporation of solvent yielded crude product as a white solid (111 g, 91.7% pure by HPLC). Recrystalisation from toluene (170 ml) yielded pure N-2,6-difluorobenzoyl-O-methylcarbamate (87 g, 81%), m.p. 123° to 123.5° C.

EXAMPLE 5

Preparation of
N-2,6-difluorobenzoyl-O-methylcarbamate

Difluorobenzamide (79 g, 0.5 mol), dimethylcarbonate (73 g, 0.8 mol) and tetrahydrofuran (200) ml were stirred together at ambient temperature (20° C.), and sodium hydride (16 g, 0.67 mol) was added. The mixture was then cooled to 0° C. and isopropanol (30 g) was added to initiate reaction. Within 12 minutes 12 liters of hydrogen had evolved, reaching 13.2 liters within 1 hour. When reaction had ceased, the reaction mixture was allowed to warm to ambient temperature (20° C.) and formic acid (31.2 g) was added. The mixture was heated to 50° C., allowed to cool to ambient temperature (20° C.) and was filtered to remove precipitated sodium formate. The resulting filtrate was evaporated to yield N-2,6-difluorobenzoyl-O-methylcarbonate as a white solid (109 g, 97%, 97% pure by HPLC, the remainder being difluorobenzamide). NMR, in $CDCl_3$, delta (ppm): 3.75,s,3H; 6.95,m,2H; 7.40,m,1H; 8.7,s,1H.

EXAMPLE 6

Preparation of
N-2,6-difluorobenzoyl-O-methylcarbamate, sodium salt 2,6-Difluorobenzamide (79 g, 0.5 mol), dimethylcarbonate (56 g, 0.6 mol) and xylene (400 ml) were stirred together at ambient temperature (20° C.), and sodium hydride (13 g, 0.54 mol) was added. Isopropanol (45 g) was added to initiate reaction and the reaction mixture was cooled to 0° C. and stirred at 0° C. for 20 hours, until hydrogen evolution ceased (12 liters of hydrogen were evolved). The reaction mixture was allowed to warm to ambient temperature (20° C.) and was filtered. The resulting white solid was washed with xylene (50 ml×3) and then with cyclohexane (50 ml×3) to give N-2,6-difluorobenzoyl-O-methylcarbamate, sodium salt (120 g, 99%). NMR, in $D_6$ acetone, delta (ppm): 3.44,s,3H; 6.80,m,2H; 7.20,m,1H.

Addition of this sodium salt to acetic acid or hydrochloric acid (e.g. 400 ml of 10% w/w aqueous acid in each case, at ambient temperature (20° C.)) gave N-2,6-difluorobenzoyl-O-methylcarbamate in quantitative yield, m.p. 123° to 123.5° C.

EXAMPLE 7

Preparation of
N-2,6-difluorobenzoyl-O-phenylcarbamate 2,6-Difluorobenzamide (48 g, 0.3 mol), diphenyl carbonate (96 g, 0.45 mol) and toluene (400 g) were stirred together at 10° C., and sodium hydride (8 g, 0.33 mol; as 16 g 50% w/w dispersion of sodium hydride in mineral oil) was added. The temperature of the reaction mixture rose spontaneously to 44° C. and the mixture grew full of solid matter. After the temperature of the reaction mixture began to fall, the precipitated solid was filtered off to give N-2,6-difluorobenzoyl-O-phenylcarbamate, sodium salt spectrum in mull ($cm^{-1}$) 3450 broad small, 3400 broad small, 2740 sharp small, 2680 sharp small, 1690 broad large, 1630 sharp small, 1550 broad large, 1240 sharp small, 1170 broad large, 1115 broad medium, 1005 sharp small, 970 sharp small, 905 sharp medium, 810 sharp small, 765 shoulder, 725 sharp medium, 695 sharp medium).

This salt was stirred in 10% w/w aqueous acetic acid (400 ml) at ambient temperature giving N-2,6-difluorobenzoyl-O-phenyl-carbamate (80 g, 95%) m.p. 149° C.

EXAMPLE 8

Preparation of
N-2,6-difluorobenzoyl-O-ethylcarbamate 2,6-Difluorobenzamide (48 g, 0.3 mol), diethylcarbonate (45 g, 0.4 mol) and cyclohexane (250 ml) were stirred together at ambient temperature (20° C.), and sodium hydride (7.5 g, 0.31 mol) was added. Ricinoleic acid (0.5 g) was added to initiate reaction. The reaction mixture was then stirred for 72 hours at ambient temperature (20° C.), after which the precipitated solid material was filtered and washed with cyclohexane to give N-2,6-difluorobenzoyl-O-ethylcarbamate, sodium salt. (IR spectrum in mull ($cm^{-1}$):3350 broad small, 3300 broad small, 3150 broad small, 1650-1500 multiple peaks, 1225 broad large, 1135 broad medium, 1045 sharp small, 1000 sharp medium, 970 sharp medium, 935 broad medium, 800-700 multiple peaks).

Treatment with aqueous acetic acid, as in Example 7, gave N-2,6-difluorobenzoyl-O-ethyl carbamate (57 g, 83%) m.p. 105° C.

EXAMPLE 9

Preparation of
N-2,6-difluorobenzoyl-O-phenylcarbamate

A mixture of 2,6-difluorobenzamide (48 g, 0.3 mol), potassium hydroxide pellets (19.68 g, 85.5%), oleic acid (1.38 g) and toluene was subjected to azeotropic distillation for 1½ hours. Diphenylcarbonate (66 g, 0.31 mol) was added, and after a further 15 minutes at distillation temperature the mixture was allowed to cool to ambient temperature. The precipitated solid was filtered off from the reaction mixture and was treated with aqueous acetic acid, as in Example 7, to give N-2,6-difluorobenzoyl-O-phenylcarbamate (64 g, 77%) mp 149° C.

EXAMPLE 10

Preparation of N-2,6-difluorobenzoyl-O-ethylcarbamate

Using a procedure analogous to that of Example 9, but substituting lithium hydroxide in place of potassium hydroxide, N-2,6-difluorobenzoyl-O-ethylcarbamate, mp 105° C., was prepared via N-2,6-difluorobenzoyl-O-ethylcarbamate, lithium salt. (IR spectrum in mull (cm$^{-1}$): 3350 broad medium, 3180 broad medium, 1650-1500 multiple peaks, 1250 broad large, 1155 broad small, 1120 broad small, 1050 broad small, 1000 sharp medium, 955 shoulder, 880 sharp small, 810-690 multiple small and medium peaks).

EXAMPLE 11

Preparation of N-2,6-difluorobenzoyl-O-methylcarbamate

Using a procedure analogous to that of Example 9, N-2,6-difluorobenzoyl-O-methylcarbamate, mp 123° to 123.5° C., was prepared via N-2,6-difluorobenzoyl-O-methylcarbamate, potassium salt. (IR spectrum in mull (cm$^{-1}$): 3370 broad small, 3160 broad small, 1670 sharp large, 1620 sharp small, 1565 broad large, 1240 broad large, 1130 sharp medium, 1030 sharp medium, 1000 sharp large, 1150 sharp medium, 840 sharp medium, 805 sharp medium, 797 shoulder, 750 sharp medium, 715 sharp medium).

We claim:

1. A process for the preparation of a N-benzoylcarbamate of the formula:

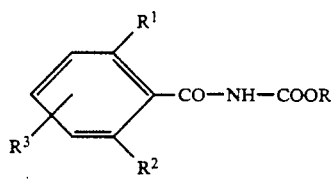 (I)

wherein R$^1$ represents a hydrogen atom, a halogen atom, a C$_{1-4}$ alkyl group, a C$_{1-4}$ alkoxy group or a trifluoromethyl group, R$^2$ represents a halogen atom, a C$_{1-4}$ alkyl group, a C$_{1-4}$ alkoxy group or a trifluoromethyl group, R$^3$ represents a hydrogen atom, a halogen atom, a methyl group or a trifluoromethyl group, and R represents a C$_{1-8}$ alkyl group optionally substituted by one or more halogen atoms or a phenyl group optionally substituted by one or more substituents selected from halogen atoms and methyl groups, said process comprising the steps of reacting an alkali metal salt of a benzamide of the formula

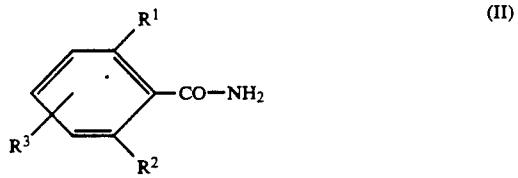 (II)

wherein R$^1$, R$^2$ and R$^3$ are as defined above, with a carbonate of the formula

 (III)

wherein R is as defined above, in the presence of an inert solvent, and neutralizing the resulting alkali metal salt of the compound of formula I.

2. A process according to claim 9 wherein R$^1$ is a hydrogen, fluorine or chlorine atom, R$^2$ is a fluorine or chlorine atom and R$^3$ is a hydrogen atom.

3. A process according to claim 1 wherein R$^1$ and R$^2$ are both fluorine atoms.

4. A process according to claim 1 wherein R is a C$_{1-6}$ alkyl group or a phenyl group.

5. A process according to claim 1 wherein the salt of the benzamide of formula II is generated using a hydride or hydroxide of lithium, sodium or potassium.

6. A process according to claim 1 wherein reaction is effected at a temperature in the range 0° C. to the distillation temperature of the reaction mixture.

7. A N-benzoylcarbamate, alkali metal salt, of general formula

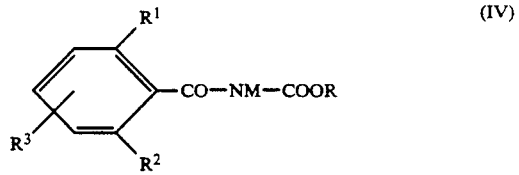 (IV)

wherein M is a lithium, sodium or potassium atom, and R$^1$, R$^2$, R$^3$ and R are as defined in claim 1.

* * * * *